(12) United States Patent
Dayton

(10) Patent No.: US 9,795,701 B2
(45) Date of Patent: Oct. 24, 2017

(54) ROOM DECONTAMINATION APPARATUS AND METHOD

(71) Applicant: Daylight Medical, Inc., Middleburg Heights, OH (US)

(72) Inventor: Roderick M. Dayton, Strongsville, OH (US)

(73) Assignee: DIVERSEY, INC., Charlotte, NC (US)

( * ) Notice: Subject to any disclaimer, the term of this patent is extended or adjusted under 35 U.S.C. 154(b) by 0 days.

(21) Appl. No.: 15/209,337

(22) Filed: Jul. 13, 2016

(65) Prior Publication Data

US 2016/0317690 A1    Nov. 3, 2016

Related U.S. Application Data

(63) Continuation of application No. PCT/US2015/051660, filed on Sep. 23, 2015.

(60) Provisional application No. 62/053,846, filed on Sep. 23, 2014.

(51) Int. Cl.
| | |
|---|---|
| *A61L 2/26* | (2006.01) |
| *A61L 2/10* | (2006.01) |
| *A61L 2/00* | (2006.01) |
| *A61L 9/00* | (2006.01) |

(52) U.S. Cl.
CPC ........ *A61L 2/26* (2013.01); *A61L 2/00* (2013.01); *A61L 2/10* (2013.01); *A61L 9/00* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,289,358 A | * | 2/1994 | Halemeier | A47B 97/00 |
| | | | | 362/269 |
| 2009/0191100 A1 | * | 7/2009 | Deal | A61L 2/10 |
| | | | | 422/105 |

FOREIGN PATENT DOCUMENTS

| | | |
|---|---|---|
| CA | 2258475 A1 | 7/1999 |
| RU | 104068 U1 | 5/2011 |
| WO | 2012122511 A1 | 9/2012 |

OTHER PUBLICATIONS

International Search Report and Written Opinion dated May 12, 2016 for PCT/US2015/051660.

* cited by examiner

*Primary Examiner* — Phillip A Johnston
*Assistant Examiner* — Hsien Tsai
(74) *Attorney, Agent, or Firm* — Cooper Legal Group, LLC

(57) ABSTRACT

Provided is a decontamination apparatus for decontaminating an enclosed room. The decontamination apparatus includes a source including a UVC bulb and a reflective shield arranged adjacent to the UVC bulb and configured to reflect UVC light emitted by the UVC bulb toward a region of the enclosed room to be decontaminated. A mounting system that is adjustable secures the source at a desired location within the enclosed room. A controller is operatively-connected to the source to terminate operation of the UVC bulb in response to a determination that an occupant is present within the enclosed room.

11 Claims, 4 Drawing Sheets

ROOM DECONTAMINATION APPARATUS AND METHOD

BACKGROUND OF THE INVENTION

1. Field of the Invention

This application relates generally to a decontamination method and apparatus and, more specifically, to an apparatus and method for emitting ultraviolet light onto surfaces of in an unoccupied room.

2. Description of Related Art

Surfaces in rooms at healthcare facilities are commonly exposed to infectious organisms and other biologically-active contaminants (hereinafter generally referred to as "contaminants") spread by the patients who occupy those rooms. These contaminants can remain viable on the contaminated surfaces to reproduce and infect others such as subsequent patients and/or visitors, for example, who enter the room and make contact with those surfaces. In an effort to prevent the spread of infections, healthcare facilities must conduct decontamination procedures in the rooms as frequently as possible.

One example of a room where contaminants are most prevalent is the bathroom located in inpatient hospital rooms. Surfaces in such bathrooms frequently come into direct contact with patients and their bodily fluids, resulting in an increased likelihood that contaminants will be present on the surfaces in bathrooms. Accordingly, the bathroom in inpatient hospital rooms should be decontaminated frequently to avoid a buildup of contaminants and minimize the risk of spreading an infection from one patient to another patient subsequently admitted to an inpatient hospital room or even a visitor or hospital personnel. However, manually decontaminating such bathrooms is labor intensive, requiring personnel to adhere to strict guidelines governing the use of liquid disinfectants. Such procedures also render the bathroom unavailable for one or more patients admitted to the corresponding inpatient hospital room for a prolonged period of time, which makes them impractical to conduct during the day when patients are most likely to use the bathroom. And conducting such decontamination procedures at night may disrupt patients, causing them to lose sleep that they may need to recover.

BRIEF SUMMARY OF THE INVENTION

According to one aspect, the subject application involves a decontamination apparatus for decontaminating an enclosed room. The decontamination apparatus includes a source including a UVC bulb and a reflective shield arranged adjacent to the UVC bulb and configured to reflect UVC light emitted by the UVC bulb toward a region of the enclosed room to be decontaminated. A mounting system that is adjustable secures the source at a desired location within the enclosed room. A controller is operatively-connected to the source to terminate operation of the UVC bulb in response to a determination that an occupant is present within the enclosed room.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
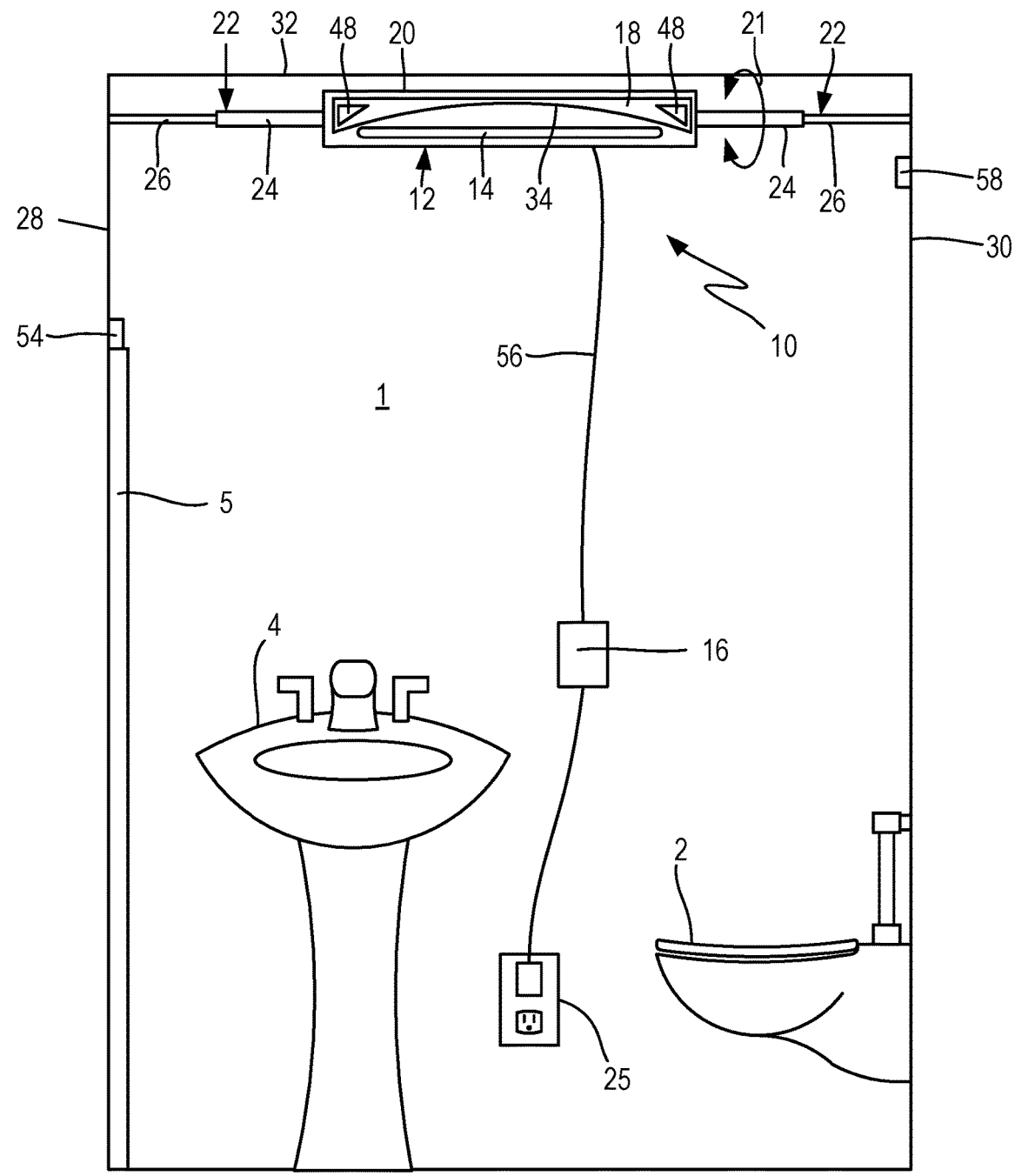
FIG. 1 shows a schematic representation of a decontamination system installed in a bathroom of an inpatient hospital room, with a portion of a housing cutaway to expose internal components.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

FIG. 1 shows an illustrative embodiment of a bathroom 1 that is accessible from an inpatient room at a hospital. The bathroom 1 includes at least a toilet 2 and a sink 4, and is accessible through a door 5 separating the inpatient room from the bathroom 1. Although not shown, the bathroom 1 can also include other fixtures and features commonly found in bathrooms, such as a shower, a bath, and/or other features commonly utilized to maintain the personal hygiene of a patient. Further, although the present disclosure focuses on the decontamination of the bathroom of an inpatient hospital room for clarity and brevity, the technology disclosed herein can be used to decontaminate the bathroom at various other public locations such as in hotel rooms, and to decontaminate rooms other than bathrooms.

Also disposed within the bathroom 1 shown in FIG. 1, is a decontamination apparatus 10 operable to at least partially decontaminate, or at least render pathogen reduced, contaminated surfaces within the bathroom 1. The decontamination process can be initiated manually, and performed by the decontamination apparatus 10 on demand and/or can be initiated automatically according to a predetermined schedule when the bathroom is unoccupied, as determined utilizing a plurality of sensors as described below.

Rendering the surfaces "pathogen reduced" with the decontamination apparatus 10 does not necessarily require the subject surfaces to be 100% sterile, free of any and all living organisms that can viably reproduce. Instead, to be considered pathogen reduced, there must be a lower level of living contagions on the decontaminated surfaces capable of reproducing or otherwise causing an infection after performance of the decontamination process than the level that existed on the surfaces prior to performance of the decontamination process. For example, the exposed surfaces in the bathroom can be considered to be pathogen reduced if at least a 1 $\log_{10}$ reduction of such contagions on the surfaces remain infectious (i.e., no more than 1/10th of the biologically-active contagions originally on the exposed surfaces remain active or infectious at a time when the decontamination process is completed) occurs. According to yet other embodiments, the surfaces can be considered pathogen reduced once at least a 3 $\log_{10}$ reduction (i.e., 1/1,000th) of such contagions on the surfaces is achieved.

Generally, the decontamination apparatus 10 includes a source 12 of a disinfecting agent, a redundant occupant sensing system that determines whether the bathroom 1 is occupied or not, and a controller 16 that interferes with emission of the disinfecting agent by the source 12 if the bathroom is occupied based on a signal from the occupant sensing system. The source 12 can be any apparatus that emits a disinfecting agent that, when exposed to the surfaces in the bathroom, renders those exposed surfaces pathogen reduced. For the illustrative embodiment shown in FIG. 1, the source 12 is an ultraviolet source that is energized to emit UVC light as the disinfecting agent.

As shown, the source 12 includes at least one, and optionally a plurality of UVC bulbs 14 coupled to a reflective shield 18 mounted within a housing 20. The housing 20 can be pivotally coupled to at least one, and optionally a plurality of mounting rods 22 or other supports that allow for pivotal adjustment of the housing 20 about a rotational axis in the directions indicated by arrow 21. At least one of the mounting rods 22 can have an adjustable length, which can be accomplished by including an external member 24 that telescopically receives an internal member 26. A spring and/or threaded member extending between the external and internal members 24, 26, or any other suitable biasing mechanism urges the internal member 26 out of the external member 24. The force exerted by the biasing mechanism is suitable in magnitude to support the housing 20 between the mounting rods 22 extending between opposing walls 28, 30 or other structures of the bathroom 1. According to alternate embodiments, brackets can extend between the ceiling 32 of the bathroom 1 and the housing 20 to suspend the housing 20 within the bathroom 1. For such installations, and any others where the decontamination apparatus 10 is added to an existing bathroom 1 instead of being installed as a built in fixture, and plugged into an electrical outlet 25 supplied by an electric power utility, the housing 20 is generally supported at an elevation vertically below the ceiling 32. However, according to alternate embodiments, the housing 20 can be integrally installed as a built-in, fixed installation at least partially recessed within the ceiling 32 (e.g., requiring adaptation or configuration of the ceiling 32 to accommodate the housing 20 as a recessed installation), and hard wired into in-wall electric circuitry and/or wiring, optionally connected to the controller 16 installed on a wall 28, 30 as a switch installation, as discussed below.

The reflective shield 18 includes an arcuate region 34 that reflects UVC light emitted upwardly from the bulbs 14 in a downward direction, generally into the bathroom 1 where the light can impinge on the surfaces to be decontaminated. The arcuate region 34 can include a curvature in multiple planes to achieve the desired light pattern for the bathroom 1. For example, the arcuate region 34 can include a plurality of regions that each have a different radius of curvature, or reflect UVC light emitted from the same source in a plurality of different directions. Accordingly, the reflected UVC light with different angles of incidence on the reflective shield 18 can be focused toward a particular region within the bathroom 1, and/or dispersed to ensure thorough coverage of the interior of the bathroom 1.

Figure 2:
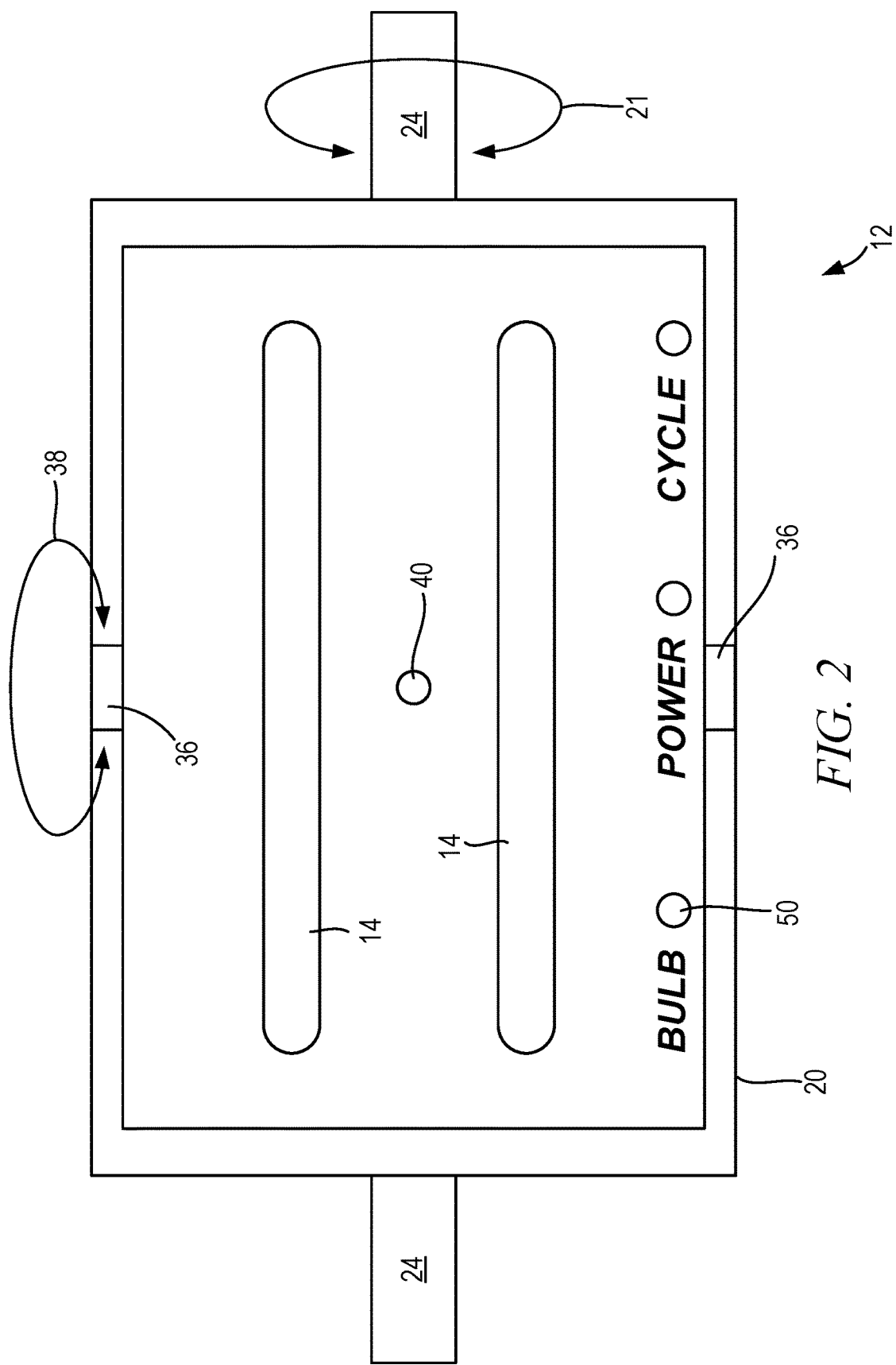
FIG. 2 is a bottom view of a source of a disinfecting agent in the form of UVC light.

As shown in FIG. 2, the reflective shield 18 can optionally be pivotally coupled to the housing 20. A post 36 extending between each side of the housing 20 and a respective side of the reflective shield establishes a rotational axis about which the reflective shield 18 can be pivoted relative to the housing 20 in the directions indicated generally by arrow 38. For such embodiments, the direction in which the UVC light is to be emitted can thus be adjusted about two, orthogonal axes of rotation (e.g., about the members 24 and about the posts 36).

To help with adjustment of the housing 20 and/or reflective shield 18, a focal indicator 40 can be provided to the reflective shield 18. Locating the focal indicator 40 between the UVC bulbs 14 as shown in FIG. 2 allows the focal indicator to identify a general direction that is representative of the direction in which the UVC light from the UVC bulbs 14 will be focused. The focal indicator 40 can include a light emitting diode ("LED"), laser light, or other optical indicator that can project light other than UVC light that will illuminate a region of a surface on which the UVC light from the UVC bulbs 14 is centered. Thus, a user can essentially aim the UVC light toward the surfaces to be rendered pathogen reduced without having to energize the UVC bulbs 14, thereby avoiding a scenario where a clinician could be exposed to the UVC light while aiming the decontamination apparatus 10. The region illuminated by the focal indicator 40 will also be subjected to the maximum UVC exposure to the UVC light emitted by the UVC bulbs 14 while the decontamination apparatus 10 is so aimed.

Figure 3:
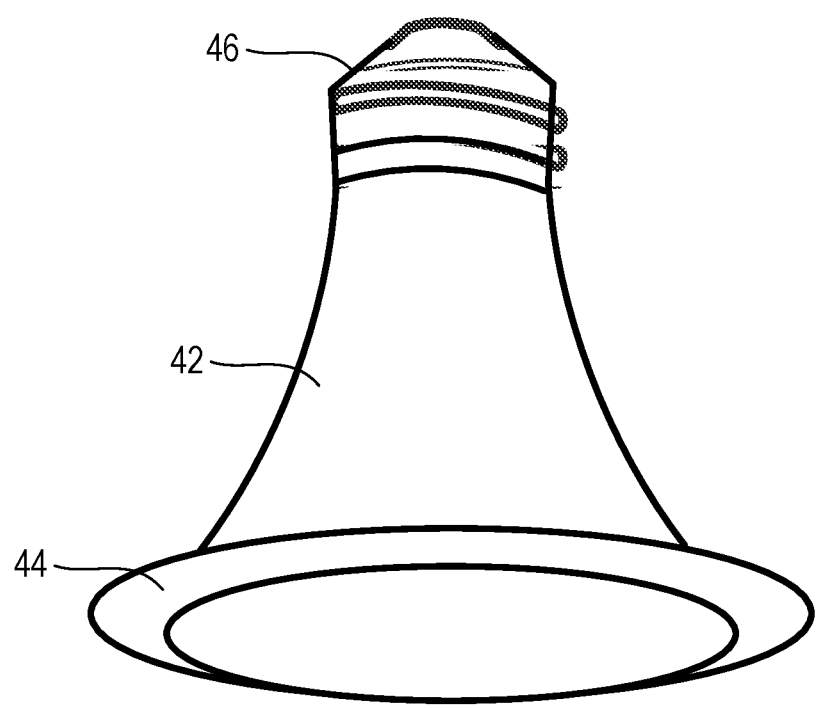
FIG. 3 is a perspective view of an alternate embodiment of a source of a disinfecting agent in the form of UVC light.

The embodiment of the source 12 shown in FIG. 2 includes a plurality of elongated, cylindrical UVC bulbs 14 that emit UVC light as the disinfecting agent. Since such a source 12 emits only UVC light, it is dedicated for performing the decontamination process described herein. Another embodiment of the source 12, shown in FIG. 3, includes both a visible-light-emitting bulb 42 such as an incandescent lamp, a fluorescent lamp and a LED lamp, for example, and a UVC bulb 44 in an annular shape. This embodiment of the source includes a screw-in base 46 such as the Edison screw, which establishes an electrical contact between a compatible utility-supplied electrical receptacle and each of the visible-light-emitting bulb 42 and the UVC bulb 44. The present embodiment of the source 12 can be screwed into existing receptacles such as recessed-light cans in the bathroom 1 as replacements for conventional bulbs. A socket insert with network communication abilities such as wireless communication abilities (e.g., IEEE 802.1x, Bluetooth, etc. . . . ), for example, can be installed between the screw-in base 46 and the existing receptacles to allow the controller 16 to control operation of the different bulbs 42, 44 provided to the present embodiment of the source. The UVC bulb 44 is to be illuminated during the decontamination process as described below, while the visible-light-emitting bulb 42 is enabled to function in a conventional manner to illuminate the interior of the bathroom 1 and allow an occupant to see objects therein.

Regardless of the configuration of the UVC bulbs 14, 44, the source 12 can optionally include an intensity sensor 48 (FIG. 1) that senses an intensity of the UVC light emitted by each UVC bulb 14, 44 present. For the sake of brevity, the present technology will be described hereinafter with reference to the elongated UVC bulbs 14, although the UVC bulbs 44 or any other desired configurations are viable alternatives. The intensity of the UVC light emitted by the UVC bulbs 14 may diminish over time. To promote thorough decontamination of the exposed surfaces in the bathroom 1 with a reasonable cycle time of a decontamination process, the intensity sensor 48 includes a photosensitive component such as a photodiode, charge coupled device, etc. . . . , that monitors the intensity of the UVC light from the UVC bulbs 14. A signal indicative of the sensed intensity is transmitted to the controller 16, which is operatively connected to at least receive signals transmitted by the intensity sensor 48 and the sensors of the redundant occupant sensing system as described below. Base at least in part on the signal from the intensity sensor 48, the controller 16 can issue a notification that one or more of the UVC bulbs 14 is nearing the end of its useful life, and should be replaced. Such a notification can include the illumination of a visible indicator in the form of a LED 50 provided to the source 12 itself, or to an appropriate LED 52 (FIG. 4) provided to the controller 16, which can be remotely located from the source 12 but in communication via a communication channel 56 such as a hardwired or wireless connection, or integrated as part of the source 12 itself. As shown in FIG. 1, the controller 16 is hardwired to the source 12 to control operation of the source 12, but is hung on a wall of the bathroom 1 at a height vertically beneath the height of the source 12 adjacent to the ceiling, where it can be reached by a clinician activating the source 12 to decontaminate the bathroom 1. According to alternate embodiments, the controller 16 can be used externally of the bathroom 1 to wireless transmit a control signal to a receiver within the bathroom 1 that is operatively connected to the source 12 to control operation of the source 12, which involves energizing and de-energizing the UVC bulbs 14 from outside the bathroom 1. For such embodiments, the remote-control version of the controller 16 transmits a control signal wirelessly that controls activation and deactivation of the UVC bulbs 14 in the bathroom 1. A switch operatively connected to the receiver provided to the source 12 selectively opens and closes the circuit(s) including the UVC bulbs 14 in response to the signals from the remote-control version of the controller 16, thereby eliminating the risk of UVC exposure to the clinician.

The redundant occupant sensing system includes a plurality of sensors that each independently senses a different property indicative of the presence or absence of a bathroom occupant. With reference once again to FIG. 1, the redundant occupant sensing system includes a door sensor 54 that is operatively connected to communicate with the controller 16, and detects a status of the door 5 as being open or closed. The door sensor 54 transmits a signal to be received by the controller 16, which can interpret the signal to determine if the door 5 is open, closed, or has changed from open to closed or closed to open. The signal can be embodied by the transmission of an electric signal over a wireless communication channel, or a hardwired connection between the door sensor 54 and the controller 16, or the interruption or establishment of a signal received by the controller 16.

Other sensors included in the redundant occupant sensing system can likewise be positioned at appropriate locations within the bathroom 1 to detect other properties that would indicate the presence or absence of an occupant. Such other sensors can be discrete sensors, or integrated into a common sensor assembly 58 as shown in FIG. 1. Each of the plurality of sensors in the redundant occupant sensing system must sense a property that the bathroom 1 is unoccupied and communicate this status to the controller 16 before the decontamination process can begin as described below. According to yet other embodiments, a plurality of, and optionally each of the sensors other than the door sensor 54 can optionally be housed within the controller 16 that is coupled to the source 12 within the bathroom 1.

An example of another of the sensors included in the integrated sensor assembly 58 of the redundant occupant sensing system is a proximity sensor that can detect the presence of an occupant without making physical contact with the occupant. The proximity sensor can utilize any suitable technology such as an electromagnetic field or electromagnetic radiation (infrared, for instance), to determine the distance of an object such as a bathroom occupant from the proximity sensor to determine whether the bathroom 1 is occupied. Such a sensor operates by monitoring the electromagnetic field or evaluating the return signal for changes, which would be indicative of the presence of a bathroom occupant. Yet other embodiments can utilize an optical sensor that relies on reflected light or the interruption of a beam of light to detect the presence of a bathroom occupant, or a capacitive sensor that senses changes in the value of a capacitance sensed within a region of the bathroom 1 where an occupant is likely to be located. Regardless of the sensing mechanism utilized, the proximity sensor signals transmitted to the controller 16 identify changes in the proximity sensor signal that indicate a change has occurred since an earlier proximity sensor signal was transmitted (e.g., when the proximity sensor was normalized under known conditions, such as when the bathroom is unoccupied).

Another sensor that can optionally be included as part of the integrated sensor assembly 58 is a sound sensor. The sound sensor can include a microphone or other sound-sensitive circuit that transmits a signal indicative of the magnitude and/or frequency of audible sounds sensed within the bathroom 1. Similar to the proximity sensor and the other sensors of the redundant occupant sensing system, the sound sensor is operatively connected to communicate with the controller 16 and transmit signals to the controller 16 that are interpretable to indicate changes in the sound level within the bathroom 1. These changes can be relative to the sound level within the bathroom 1 at a time of an earlier sound level is measured, or when the sound sensor is normalized such as when the system is powered on when the bathroom is knowingly unoccupied.

A light sensor can also optionally be included as part of the sensor assembly 58 to detect changes in light within the bathroom 1. The light sensor can include a photosensitive component such as a photodiode, charge coupled device, etc. . . . , that monitors the intensity of visible light and/or UVC light within the bathroom. Again, a signal indicative of the sensed light levels within the bathroom 1 is transmitted to the controller 16, which can determine whether a change in light level has occurred, which would suggest an occupant has entered the bathroom 1.

Further, a motion sensor can also optionally be included in the sensor assembly 58 to sense movement within the bathroom 1. Such sensors can be sense a property such as changes in the thermal signature at various locations within the bathroom 1. Utilizing the temperature gradients to detect motion is advantageous in that inanimate movement in the bathroom (e.g., a towel falling from a rack) will not trigger the motion sensor to transmit a signal indicative of movement. Other embodiments of the motion sensor include a photoelectric sensor that utilizes a beam of light or and laser that travels from a source to a detector. When an occupant crosses the path of light, the light is blocked and the sensor detects the obstruction. Such motion sensors can optionally be positioned at particularly revealing locations such as approximately 1-3 ft. above the floor at the door 5. Projecting a beam of light at such a location will almost certainly be broken if an occupant enters the bathroom 1 through the door 5.

Certain embodiments of the decontamination system will include at least one of the aforementioned sensors (door, proximity, sound, light and movement), and optionally a plurality, or all of these sensors. However, alternate embodiments can utilize any other suitable sensor(s) that can transmit a signal indicative of the presence of a living occupant within the bathroom 1 without departing from the scope of the present disclosure. For example, a carbon dioxide sensor can be utilized to sense a change in the carbon dioxide level in the bathroom 1 cause by an occupant exhaling. Other embodiments can utilize a heartbeat monitor that can remotely sense the impulses of a beating heart without making physical contact with an occupant. Yet other embodiments can utilize a pressure sensor operatively connected to the toilet 2 to sense when an occupant is seated thereon, or a water sensor to sense when a valve provided to the sink 4 has been opened to allow water to run.

Figure 4:
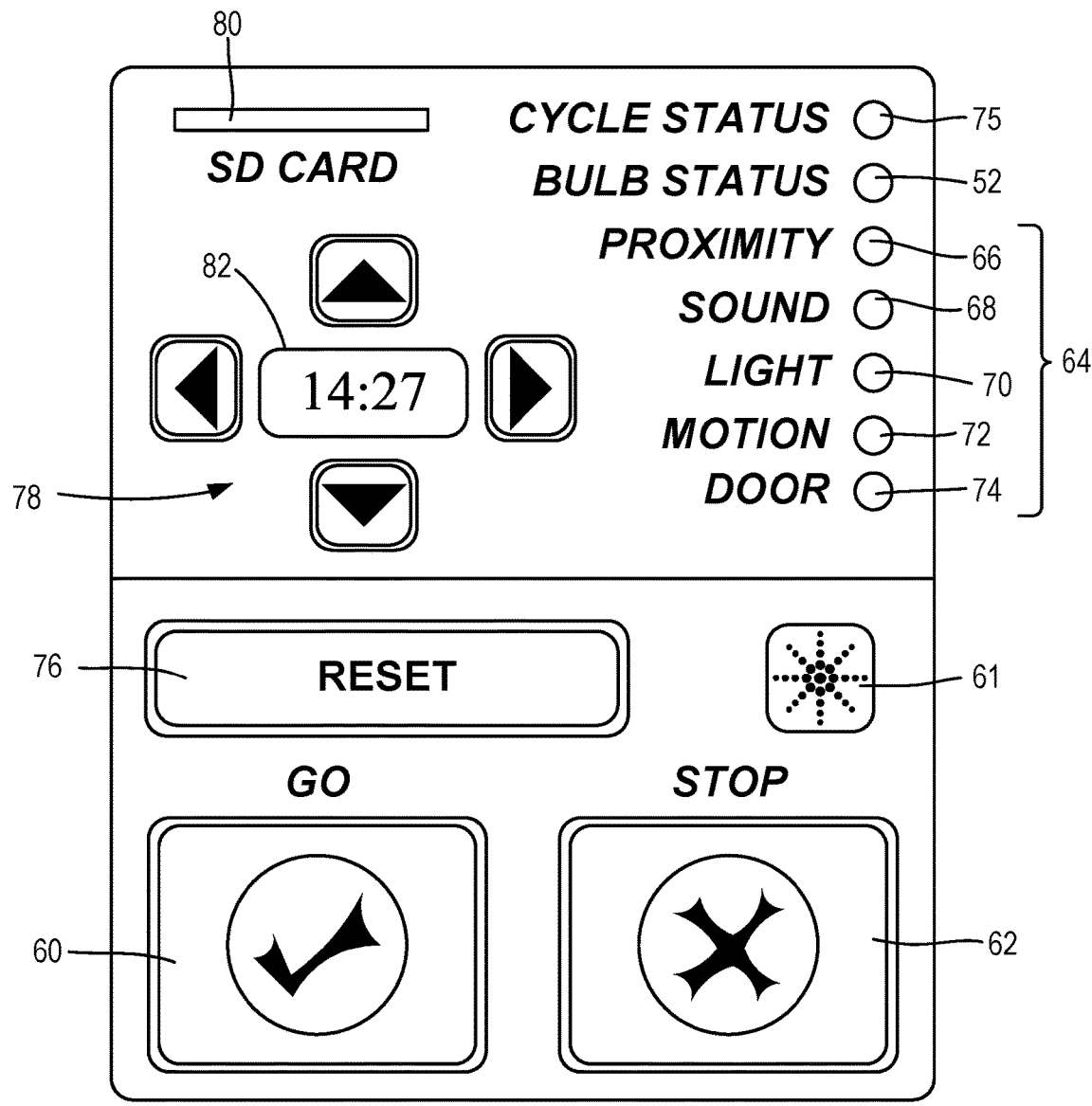
FIG. 4 is a front view schematically depicting a controller of a decontamination system.

An illustrative embodiment of the controller 16 is shown in FIG. 4. As shown, the controller 16 includes manual override buttons 60, 62 that, when pressed, cause the decontamination process to be manually initiated and stopped on demand, respectively. If the start button 60 is selected, the controller 16 implements a delay of a predetermined duration (e.g., 10 seconds) that is sufficient to allow the person who pressed the start button 60 to exit the bathroom 1 before the UVC bulbs 14 are illuminated as part of the decontamination process. An audible warning such as a repeating beep can be broadcast by a speaker 61 provided to the controller 16 to warn of the impending start of the decontamination process.

Following the expiration of the delay, each of the sensors included in the redundant occupant sensing system is normalized, indicating a state where it is assumed that the bathroom 1 is unoccupied. If, at any time during the decontamination process any of the sensors senses a property that is indicative of a change from the state in which the sensors were normalized, the controller 16 determines that the bathroom has become occupied, and immediately terminates the decontamination process. To identify the cause of termination, one or a plurality of labeled visible indicators 64 such as discrete LEDs, a liquid crystal display ("LCD"), or any other suitable notification device provided to the controller 16 can be activated. For example, the proximity indicator 66 can be illuminated to indicate that the proximity sensor triggered termination; the sound indicator 68 can be illuminated to indicate that the sound sensor triggered termination; the light indicator 70 can be illuminated to indicate that the light sensor triggered termination; the motion indicator 72 can be illuminated to indicate that the motion sensor triggered termination; and the door indicator 74 can be illuminated to indicate that the door sensor 54 triggered termination. The specific visible indicators 64 included as part of the controller 16 can correspond to the specific sensors present.

If premature termination of the decontamination process occurs before the decontamination process is complete (e.g., before the UVC bulbs 14 have been illuminated for the time required to achieve the desired level of pathogen reduction), a cycle status indicator 75 can be illuminated in a manner indicative of such termination. For example, the cycle status indicator 75 can be illuminated red, and/or made to flash to call an operator's attention to the premature termination of the decontamination process. The manual pressing of a reset button 76 can be required by the controller 16 before the decontamination process can be restarted. Requiring the reset button 76 to be pushed will allow an operator to ensure that the condition resulting in termination of the decontamination apparatus has been cleared before resetting the controller 16.

Premature termination of the decontamination apparatus can be saved in a log stored on a computer-readable medium (e.g., SD card inserted into SD card port 80 provided to the controller 16, built in hard drive or other non-transitory computer-readable medium provided to the controller 16, remote hard drive or other non-transitory medium remotely located over a hospital communication network) in communication with the controller 16. Such a log can maintain data concerning the cause of an interruption, a time of an interruption, a time since the last successfully-completed decontamination process, and any other data pertaining to the decontaminated state of the bathroom 1. Such data can be utilized to diagnose problems such as a faulty sensor included in the redundant occupant sensing system, and to promote regular decontamination of the bathroom 1.

The controller 16 can optionally be configured to restart a prematurely-terminated decontamination cycle without manual user intervention. For example, once all of the conditions sensed by the sensors in the redundant occupant sensing system return to their normalized values, the controller 16 can initiate a timer to establish a restart delay. If all of the conditions remain at their normalized values for the duration of the restart delay, the controller 16 can automatically restart the decontamination process by once again activating the UVC bulbs 14 for the predetermined cycle time. This process of restarting the decontamination process can optionally be repeated until the decontamination process has been completed successfully.

In the absence of any conditions interrupting the decontamination process, the decontamination process will remain active, with the UVC bulbs 14 illuminated and the redundant occupant sensing system monitoring conditions within the bathroom 1 for any changes that would indicate an occupant has entered for a predetermined cycle time. The predetermined cycle time can be manually input and programmed into the controller 16 via a timer input system 78 provided to the controller 16, or can be established through an administration terminal and delivered to the controller 16 via a portable computer-readable medium such as an SD card inserted into an SD card slot 80 provided to the controller 16. According to alternate embodiments, actions such as adjusting the duration of the decontamination process and actions other than manually initiating the decontamination process can be carried out over a communication network from a remotely-located administration terminal. The cycle time can be independently established to a custom duration for each bathroom 1 depending on factors such as the size of the bathroom, the number and intensity of the UVC bulbs 14 to be utilized, the distance separating the source 12 from the surfaces to be decontaminated, etc. . . . to achieve the desired level of decontamination to be achieved. According to alternate embodiments, a default value that can be used for most installations can be utilized. The default value can be selected to be "overkill", meaning that the default duration will be longer than required to achieve the desired level of decontamination for most installations based, at least in part, on assumptions about the size of the bathroom, the number and intensity of the UVC bulbs 14 to be utilized, the distance separating the source 12 from the surfaces to be decontaminated, etc. . . .

Once the decontamination process has been successfully completed, the cycle status indicator 75 can be illuminated as a solid (i.e., non-flashing) green color or otherwise notify an observer that the decontamination process has been successfully completed. Additionally, successful completion of the decontamination process can be logged on the computer-readable medium in communication with the controller 16, documenting a time when the bathroom was last successfully decontaminated.

The manual procedure of initiating and conducting a decontamination process described above can be one of a plurality of operational modes. The decontamination system 10 can also optionally be configured to conduct a decontamination process according to a defined schedule. For example, a timer 82 provided to the controller 16 can be programmed to initiate the decontamination process at a set time, such as 1:00 AM, local time. At that set time, the decontamination process can proceed as described above for the manually-initiated process.

Another configuration of the controller 16 includes using the timer 82 to define a window of time during which the controller 16 will allow the decontamination process to be initiated. For example, the timer 82 can be programmed to allow the decontamination process to be initiated only between the hours of midnight and 5:00 AM, local time, each night. Thus, even if the start button 60 is pressed outside of this window, the controller 16 will not initiate the decontamination process. But within the permissible window of operation, the decontamination process can be initiated manually, and/or the redundant occupant sensing system can continuously monitor conditions within the bathroom 1 to determine when the bathroom has been unoccupied for at least a predetermined period of time (e.g., for at least 10 minutes). Once such a delay has expired, the decontamination process can be automatically initiated by the controller 16.

The decontamination system 10 can also optionally be configured to initiate a decontamination process at a predetermined frequency, and/or based on usage of the bathroom 1. For example, the controller 16 can be configured to initiate a decontamination process every X hours, where X can be any desired period of time such as 8 hours, 24 hours, 48 hours, etc. . . . , conditioned on the premise that the redundant occupant sensing system determines the bathroom 1 is unoccupied. As an example of decontamination based on bathroom usage, the redundant occupant sensing system can continuously monitor the status of the bathroom 1 from a time at which the decontamination system is powered up. When an occupant enters the bathroom 1, the changes sensed by the redundant occupant sensing system will indicate that the bathroom 1 is occupied. However, the changes will eventually revert to their normalized values once the occupant leaves the bathroom 1. In response to determining the occupant has left based on the signals from the redundant occupant sensing system, or after a predetermined time has elapsed since the controller 16 determined the occupant has left the bathroom 1, the controller 16 can initiate a decontamination process. Such a use-based example can also optionally be restricted to occur only during a permissible window of time such as that described above.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A decontamination apparatus for decontaminating an enclosed room, the decontamination apparatus comprising:
   a source comprising a UVC bulb and a reflective shield arranged adjacent to the UVC bulb and configured to reflect UVC light emitted by the UVC bulb toward a region of the enclosed room to be decontaminated;
   a mounting system that is adjustable to secure the source at a desired location within the enclosed room; and
   a controller operatively-connected to the source to terminate operation of the UVC bulb in response to a determination that an occupant is present within the enclosed room, wherein
   the reflective shield comprises a plurality of regions, each of the plurality of regions having a different arcuate shape comprising a different radius of curvature to reflect the UVC light emitted by the UVC bulb toward the region of the enclosed room to be decontaminated.

2. The decontamination apparatus of claim 1 further comprising a housing in which the UVC bulb and the reflective shield are mounted, the housing being adjustably coupled to pivot about a first axis of rotation.

3. The decontamination apparatus of claim 2, wherein the housing comprises a coupling that adjustably supports the UVC bulb to pivot about a second axis of rotation that is substantially perpendicular to the first axis of rotation.

4. The decontamination apparatus of claim 2 further comprising a focal indicator that emits light other than the UVC light to illuminate a target portion of the enclosed room that will be subjected to maximum exposure of the UVC light, wherein a direction in which the light other than the UVC light is emitted from the focal indicator is adjustable as a result of adjustment of the housing.

5. The decontamination apparatus of claim 4, wherein the focal indicator comprises a light source comprising at least one of a light emitting diode and a laser light.

6. The decontamination apparatus of claim 1 further comprising a door sensor operatively connected to transmit a signal to the controller indicative of a state of a door leading into the enclosed room, wherein the controller is configured to determine that the occupant is in the enclosed room and terminate operation of the UVC bulb based on the signal transmitted by the door sensor.

7. The decontamination apparatus of claim 6 further comprising a redundant occupancy sensing system operatively connected to transmit an occupant signal to the controller, the redundant occupancy sensing system comprising at least one additional occupant sensor that senses a property indicative of the occupant's presence within the enclosed room and transmits the occupant signal to the controller in response, thereby causing the controller to terminate operation of the UVC bulb.

8. The decontamination apparatus of claim 7, wherein the at least one additional occupant sensor comprises at least one of: a proximity sensor, a sound sensor, a light sensor, and a motion sensor.

9. The decontamination apparatus of claim 7, wherein the at least one additional occupant sensor comprises two or more of: a proximity sensor, a sound sensor, a light sensor, and a motion sensor.

10. The decontamination apparatus of claim 1, wherein the support member comprises an adjustable length to extend between the surface of the enclosed room and the housing, and the mounting system further comprises a biasing mechanism that exerts a force against the surface of the enclosed room to maintain a position of the housing at an elevation vertically beneath a ceiling of the enclosed room.

11. The decontamination apparatus of claim 1 further comprising a plug that is to be plugged into a wall outlet in the enclosed room, the wall outlet being supplied by an electric power utility.

\* \* \* \* \*